United States Patent
Yeh et al.

(10) Patent No.: US 8,546,114 B2
(45) Date of Patent: Oct. 1, 2013

(54) PROCESSES FOR THE PREPARATION OF OPTICALLY ACTIVE CYCLOPENTENONES AND CYCLOPENTENONES PREPARED THEREFROM

(75) Inventors: Yu-Chih Yeh, Taipei (TW); Ming-Kun Hsu, Longtan Township, Taoyuan County (TW); Shih-Yi Wei, Taipei (TW)

(73) Assignee: Chirogate International Inc., Ping-Cheng, Taoyuang Hsien (TW)

( * ) Notice: Subject to any disclaimer, the term of this patent is extended or adjusted under 35 U.S.C. 154(b) by 460 days.

(21) Appl. No.: 11/334,336

(22) Filed: Jan. 18, 2006

(65) Prior Publication Data

US 2007/0166809 A1 Jul. 19, 2007

(51) Int. Cl.
- C07C 35/06 (2006.01)
- C07C 35/00 (2006.01)
- C12P 7/62 (2006.01)
- C12N 9/20 (2006.01)
- C12P 31/00 (2006.01)
- C07C 405/00 (2006.01)

(52) U.S. Cl.
USPC ........... 435/135; 435/280; 435/198; 568/300; 568/838; 554/117

(58) Field of Classification Search
None
See application file for complete search history.

(56) References Cited

U.S. PATENT DOCUMENTS

| 3,723,423 | A | * | 3/1973 | Andersen et al. | 549/415 |
| 4,066,692 | A | * | 1/1978 | Cragoe et al. | 514/560 |
| 4,536,592 | A | | 8/1985 | Collins et al. | |
| 5,075,478 | A | * | 12/1991 | Behling et al. | 556/441 |
| 5,080,795 | A | * | 1/1992 | Pirkle et al. | 210/643 |
| 6,852,880 | B2 | | 2/2005 | Ham et al. | |
| 2005/0154220 | A1 | | 7/2005 | Clissold et al. | |
| 2005/0209337 | A1 | | 9/2005 | Gutman et al. | |
| 2006/0079693 | A1 | | 4/2006 | Suen et al. | |

FOREIGN PATENT DOCUMENTS

| EP | 0 357 009 | 3/1990 |
| WO | 93/00329 | 1/1993 |
| WO | 02/096898 | 12/2002 |
| WO | 2006/112742 | 10/2006 |

OTHER PUBLICATIONS

Lola, D.O; Freimanis, J.F.; Vosekalna, I. A.; Liepina, A.Y. "Preparation and chiroptical properties of enantiomers of hydroxy derivatives of cyclopentenone" Z.Org.Khim. 1988, 24(7), 1422-1428.*
Green, Theodora and Wuts, Peter G.M. Protective Groups in Organic Chemistry. John Wiley and Sons, Inc. 1999, pp. 1-21, 369-442, 701-715, and 728-731.*
Lola, D.O; Freimanis, J.F.; Vosekalna, I. A.; Liepina, A.Y. "Preparation and chiroptical properties of enantiomers of hydroxy derivatives of cyclopentenone" Z.Org.Khim.(international/English Edition), 1988, 24(7), pp. 1280-1285.*
Veinberga, I. and Freimanis, J. "Preparation of optically active 2-alkoxycarbonylmethyl-4-hydroxy-2-cyclopenten-1-one by enzymic hydrolysis -dependence of hydrolysis enantioselectivity on the structure of substrate" Latvijas Kimijas Zurnals (1995), (1-2), pp. 116-119.*
Lola, D., et al. "Synthesis of 2-methoxy(alkoxy)carbonylmethyl-2-cyclopenten-1-one 4-alkoxy derivatives" Latvijas PSR Zinatnu Akademijas Vestis, Kimijas Serija.1988,(5), pp. 602-610.*
Veinberga, I. and Freimanis, J. "Preparation of optically active 2-alkoxycarbonylmethyl-4-hydroxy-2-cyclopenten-1-one by enzymic hydrolysis -dependence of hydrolysis enantioselectivity on the structure of substrate" Latvijas Kimijas Zurnals (1995), (1-2), pp. 116-121.*
Davanakov, V.A. "Analytical Chiral Separation Methods" Pure and Applied Chemistry, 1997,69(7), pp. 1469-1474.*
Veinberga, I. et al. "Comparison of Enzymic Hydrolysis and Synthesis of Esters of Optically Active . . . " Bioorganicheskaya Khimiya (1991) vol. 17, No. 6, pp. 760-766, retrieved from STN, XP-002390158 (CAS Abstract Only).
Pinot, E. et al. "Enzymatic Kinetic Resolution of a Functionalized 4-Dydroxy-Cyclopentenone: Synthesis of the Key Intermediates in the Total Synthesis of Isoprostanes" Tetrahedron: Asymmetry (2005) vol. 16, No. 11, pp. 1893-1895.
Grognux, J. et al. "Universal Chromogenic Substrates for Lipases and Esterases" Tetrahedron: Asymmetry (2004) vol. 15, No. 18, pp. 2981-2989.
Veinberga, I. et al. "Preparation of Optically Active 2-Alkoxycarbonylmethyl-4-Hydroxy-2-Cyclopenten-I-One by Enzymic . . . " Latvijas Kimijas Jurnals (1995) 1-2, pp. 116-121, retrieved from STN, XP-002399673(CAS Abstract Only).
Lola, D. et al. "Synthesis of 2-Methoxy (Alkoxy) Carbonylmethyl-2-Cyclopeneten-1-One-4-Alkoxy Derivatives." Latvijas PSR Zinatnu Akademijas Vestis, Kimijas Serija (1998) vol. 5, pp. 602-610, XP-002399674(CAS Abstract Only).
Loza, E. et al. "Synthesis and Properties of 5-hetero-6-ketoprostaglandins El. 1. Ester Derivatives of 4 . . . " Latvijas PSR Zinatnu Akademijas Vestis, Kimijas Serija (1989) vol. 2, pp. 234-242, XP-002399675 (CAS Abstract only).
Noyori, R., et al. "Prostaglandin Syntheses by Three-Component Coupling." Angew Chem. Int. Ed. Engl. (1984) vol. 23, pp. 847-876.
Sato, F., et al. "Prostaglandin Synthesis via Two-Component Coupling. Highly Efficient Synthesis of Chiral Prostaglandin Intermediates a-Alkoxy-2-alkyl-2-cyclopenten-1-one and 4-Alkoxy-3-alkenyl-2-methylenecyclopentan-1-one." J. Org. Chem. (1988) vol. 53, pp. 5590-5592.
Lola (Zh. Org. Khim) (1985) vol. 21, No. 10, pp. 2091-2101.

(Continued)

Primary Examiner — Chris R Tate
Assistant Examiner — Aaron J Kosar
(74) Attorney, Agent, or Firm — Ladas & Parry LLP

(57) ABSTRACT

The present invention relates to novel processes for preparing optically active Cyclopentenones of Formula (R)-1,

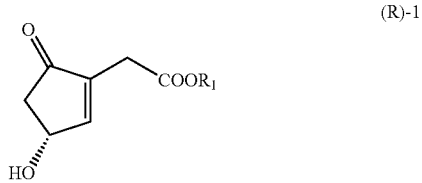

which are useful for the preparation of Prostaglandins and analogs thereof. The invention also relates to novel Cyclopentenones prepared from the processes.

16 Claims, No Drawings

(56) References Cited

OTHER PUBLICATIONS

Noyori, R., et al. "The Three-Component Coupling Synthesis of Prostaglandins." *J. Am. Chem. Soc.* (1988) vol. 110, pp. 4718-4726.

Sih, C. J., et al. "Asymmetric Total Synthesis of (−)-Prostaglandin $E_1$ and (−)-Prostaglandin $E_2{}^1$." *Journal of the American Chemical Society* (1975) 97:4, pp. 865-874.

Baraldi, P. G., et al. "Stereospecific Nitromethane Conjugate Addition to 4-Oxygenated-2-Substituted-Cyclopent-2-Enones: A Simple Approach to Prostaglandins." *Tetrahedron* (1987) vol. 43, pp. 4669.

Green. T. W., et al. "Protective Groups in Organic Synthesis ($3^{rd}$ Edition)." *Carbohydrate Polymers 45* (2001) 105-108.

Loza, E., et al. "Enantiomeric enrichment of partially resolved 4-hydroxy-2-carboxymethylcyclopentanone derivatives by achiral phase chromatography." *Journal of Chromatography A* (1995) vol. 708, pp. 231-243.

Mar., J. "Aliphatic Nucleophilic Substitution / Reactions." in *March, Jerry, Advanced Organic Chemistry Reactions, Mechanisms and Structure*, Third Edition (1985) pp. 350-351.

Office Action dated Jul. 24, 2012 for Application No. JP 2007-009402 and English translation.

Corral, C., et al., "The Pyrethrins and Related Compounds VII.*— New Pyrethrin-like Compounds with Ester and Ketonic Groups in the alcoholic Side Chain", J. Sci. Fd. Agric. 1965, vol. 16, September, pp. 514-518.

Kim. Seongjin. et al. "Synthesis of 15R-$PGD_2$: a potential $DP_2$ receptor agonist." Bioorganic & Medicinal Chemistry Letters 15 (2005) 1873-1875.

Bowler. Jean. et al. (1974) "Reduction of Prostagladin Enone Intermediates with Aluminum Isopropoxide" Synthetic Communications, 4:4, 211-213.

Corey. E.J.. et al. "A Stable and Easily Prepared Catalyst for the Enantioselective Reduction of Ketones. Applications to Multistep Syntheses". J. Am. Chem. Soc. 1987. 109. 7925-7926.

Corey, E.J., et al. Stereo-Controlled Synthesis of Prostaglandins $F_{2\alpha}$ and $E_2$ (dl). Communications to the Editor. Journal of the American Chemical Society, 91:20, Sep. 24, 1969.

\* cited by examiner

PROCESSES FOR THE PREPARATION OF OPTICALLY ACTIVE CYCLOPENTENONES AND CYCLOPENTENONES PREPARED THEREFROM

FIELD OF THE INVENTION

The present invention relates to novel processes for preparing optically active Cyclopentenones of Formula (R)-1,

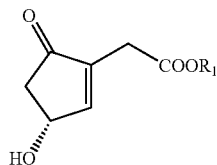
(R)-1 which are useful for the preparation of Prostaglandins and analogs thereof. The invention also relates to novel Cyclopentenones prepared from the processes.

BACKGROUND OF THE INVENTION

Prostaglandins and the derivatives thereof have various biological actions, such as a vasodilating action, a prophlogistic action, an inhibitory action of blood platelet aggregation, a uterine muscle contraction action, an intestine contraction action and a lowering action of intraocular pressure, and can be used in the preparation of medicaments for treatment or prevention of myocardial infarction, angina pectoris, arteriosclerosis, hypertension, or duodenal ulcer, which are valuable for human as well as veterinary applications.

For the last few decades, many academic researchers and industrial organizations have made tremendous efforts in exploring various key intermediates as well as innovative processes for efficient and cost-saving synthesis of Prostaglandins (Collines, P. W. et. al., 1993, Chem. Rev. 93, 1533).

Lolja, D., et al. reported that Cyclopentenones of Formula (R)-1,

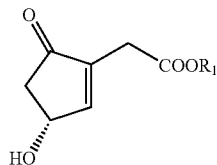
(R)-1 wherein $R_1$ is an unsubstituted straight and saturated alkyl, are potential intermediates in the synthesis of Prostaglandins (Lolja, D., et al., Zh. Org. Khim 1985, 21(4), 782). As depicted in Scheme 1 shown below, Beraldi, P. G., et al. converted Cyclopentenone of Formula (R)-1, wherein $R_1$ is methyl, using a nitromethane conjugate addition method, to Corey aldehyde of Formula II, which is an advanced key intermediate in the synthesis of Prostaglandins (Beraldi, P. G., et al., 1987, Tetrahedron, 43, 4669).

Scheme 1

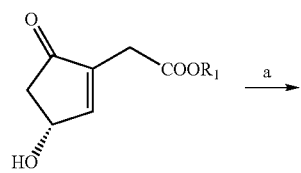

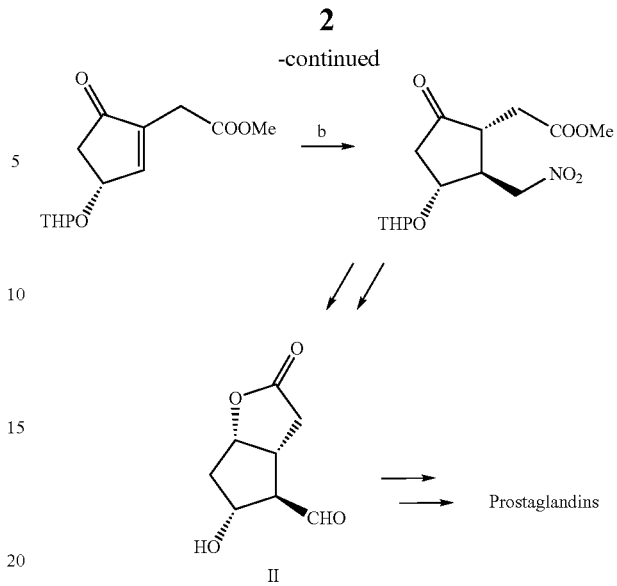

Beraldi, P. G., et al. employed a method, as shown below in Scheme 2, for preparing the optically active cyclopentenone of (R)-1, wherein $R_1$ is methyl, in which a diastereomeric oximes is formed by reacting the racemic mixture with a chiral agent (R)-2-aminoxy-4-methylvaleric acid and the desired form of Formula (R)-1 is isolated and obtained from a column separation.

Scheme 2

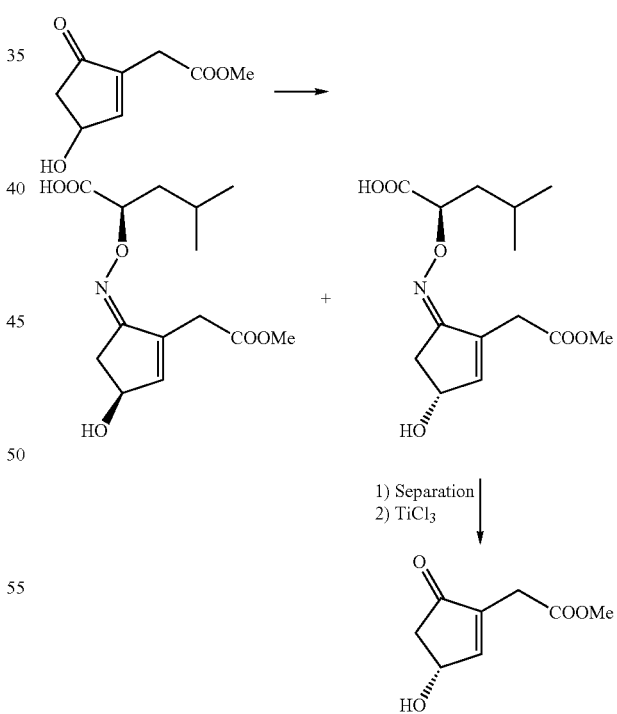

Unfortunately, the two isomers in the diastereomeric oximes produced in the Beraldi's method have structures and properties similar to each other and therefore it is extremely difficult to separate them from each other to obtain the desired product with the desired optical purity using a column chromatography. Moreover, about a half of the compounds that existed as the unwanted isomer is wasted. It seemed that Beraldi's method is not quite economical due to aforementioned reasons.

Alternatively, Veinberga, I. et. al. utilized various enzymatic methods including enzymatic hydrolysis (Latv. Kim. Z. (1-2), 122, 1995 and Latv. Kim. Z. (1-2), 116, 1995) and a two-step enzymatic reaction (Latv. Kim. Z. (1), 103, 1992) to obtain an optically active cyclopentenone of Formula (R)-1 wherein $R_1$ is exclusively methyl. Unfortunately, none of these enzymatic reactions or biocatalysts used by Veinberga, I. et. al. exhibits potential optical selectivity toward the substrates. Therefore, the preparation of an optically active cyclopentenone with an optical purity higher than 85% e.e. (enatiomeric excess) is difficult to be achieved.

In another aspect, conjugate addition approach has been employed to build up the stereochemistry of Prostaglandin cyclopentanes. During the process of the conjugation addition, two new chiral centers are formed as depicted in Scheme 3.

Scheme 3

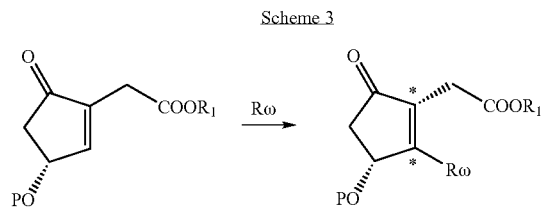

In spite that the reaction is in favor of forming the three substituents on the cyclopentane ring respectively in trans orientation due to kinetic equilibrium, the stereoisomers with cis orientation are inevitably formed. The critical concern has been focused on how to remove the stereoisomers left in the conjugated products or how to reduce the stereoisomers generated during the conjugation addition process. In order to facilitate the removal of these stereoisomers, it is anticipated that RI should render the crystallinity of the compounds higher so as to enable easy separation of cis isomers from the conjugated products by crystallization. Alternatively, it is suggested to employ cyclopentenone (R)-1 having bulkier substituents to proceed the reaction in that a bulkier $R_1$ will minimize the generation of the cis isomers. Unfortunately, conventional technology related to cyclopentenone (R)-1 has been confined to $R_1$ being unsubstituted straight and saturated alkyl groups which either are non-bulky or have poor crystallinity. Studies concerning $R_1$ being bulky alkyl, aryl, or aralkyl groups have never been investigated before.

SUMMARY OF THE INVENTION

The present invention provides novel processes of preparing optically active Cyclopentenones (R)-1 without the drawbacks encountered by conventional processes. More importantly, the processes disclosed herein are easier to be practiced and economical and useful for industrial production purposes. Furthermore, the invention also provides novel cyclopetenones with a broader range of selections on the ester functional groups by introducing a novel $R_1$ group that is bulkier or results in higher crystallinity of the optically active Cyclopetenones (R)-1.

DETAILED DESCRIPTION OF THE INVENTION

I. Definition

The term "alkyl" used herein refers to a straight or branched hydrocarbon group containing 1 to 30 carbon atoms, such as methyl, ethyl, isopropyl, tert-butyl, and the like; or a cyclic saturated hydrocarbon group having 3 to 10 carbon atoms, such as cyclopropyl, cyclopentyl, cyclohexyl, menthyl, and the like.

The term "lower alkyl" used herein refers to an alkyl containing 1 to 6 carbon atoms such as methyl, ethyl, propyl, and the like.

The term "alkenyl" used herein refers to a straight or branched hydrocarbon group containing 3 to 20 carbon atoms and one or more carbon-to-carbon double bonds, such as pentenyl, propenyl, and the like; or a cyclic unsaturated hydrocarbon group having 5 to 20 carbon atoms and one or more carbon-to-carbon double bonds, such as cyclopentenyl, cyclohexenyl, and the like.

The term "alkynyl" used herein refers to a straight or branched hydrocarbon group containing 3 to 20 carbon atoms and one or more carbon-to-carbon triple bonds such as pentynyl, propynyl, and the like; or a cyclic unsaturated hydrocarbon group having 6 to 20 carbon atoms and one or more carbon-to-carbon triple bonds.

The term "aryl" used herein refers to a monocyclic or polycyclic aromatic hydrocarbon radical, such as phenyl, naphthyl, anthryl, phenanthryl and the like. The aryl may optionally be substituted with one or more substituents, including but not limited to, a halogen, an alkoxyl, a thioalkoxyl, an alkyl, and an aryl.

The term "aralkyl" used herein refers a straight or branched hydrocarbon containing 1 to 20 carbon atoms and one or more aryl group as described above, such as benzyl, benzhydryl, fluorenylmethyl, and the like.

Each of the above mentioned alkyl, alkenyl, alkynyl, aryl, and aralkyl may optionally be substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrrolidinonyl, and the like.

The term "protective group" has the meaning conventionally defined in organic synthetic chemistry, i.e., a group capable of protecting a functional group or moiety of a compound against the attacks of a chemical reaction. Examples of the protective group include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_aR_bR_c$ wherein $R_a$, $R_b$ and $R_c$ are each independently a $C_{1-4}$ alkyl, phenyl, benzyl, a substituted phenyl, or a substituted benzyl.

In the depiction of the compounds given throughout this description, a thickened taper line (━) indicates a substituent which is in the beta-orientation(above the plane of the molecule or page), a broken flare line (⋯⋯) indicates a substituent which is in the alpha-orientation (below the plane of the molecule or page).

II. First Aspect of the Invention

II-1 Process for Preparing Racemic Cyclopentenones of Formula 1

Cyclopentenones of Formula 1 wherein $R_1$ is an alkyl, an alkenyl, an alkynyl, an aryl, or an aralkyl, each of which is unsubstituted or substituted with one or more substituents selected from the group consisting of halogen, alkyl, aryl, alkoxyl, aryloxy, thioalkoxy, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl and pyrrolidinonyl, or a protective group for the carboxyl group, are prepared from 2-furaldehyde, as shown in Scheme A.

Cyclopentenones of Formula 1 wherein $R_1$ is as defined above can also be prepared from Cyclopentenones of Formula 1' wherein $R_2$ is a lower alkyl by transesterification.

According to the invention, the transesterification of cyclopentenones of Formula 1' to Formula 1 is shown in Scheme B.

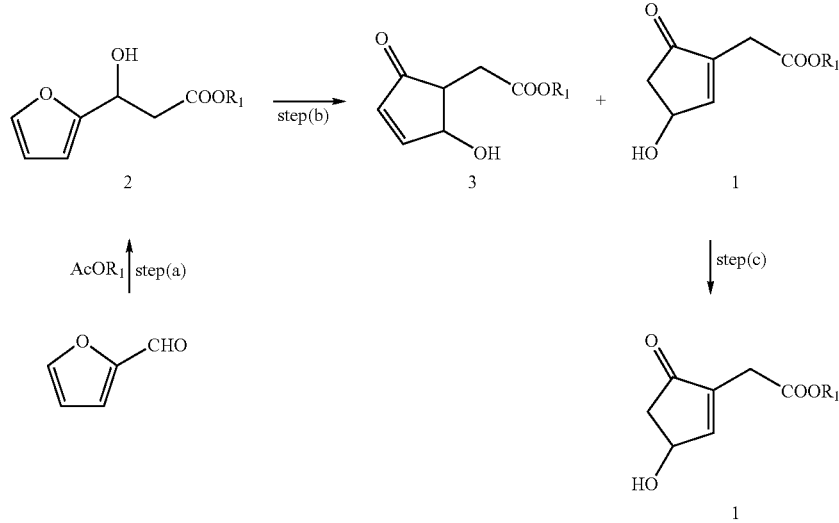

In Step (a) of Scheme A, 2-furaldehyde is reacted with a compound of Formula $AcOR_1$ wherein $R_1$ is as defined above to obtain furancarbinols of Formula 2.

In Step (b), furancarbinols of Formula 2 are transformed (or rearranged) to obtain a mixture of cyclopentenones of Formulae 3 and 1. In Step (c), the mixture is further subjected to an isomerization reaction to convert the cyclopentenones of Formula 3 into the cyclopentenones of Formula 1.

In Scheme A, Step (a) is an aldol condensation reaction between 2-furaldehyde and the compound of Formula $AcOR_1$, wherein $R_1$ is as defined above, which can be conducted in the presence of a base, preferably lithium diisopropyl amide (LDA). Step (b) is a transformation (i.e., rearrangement) reaction, which can be carried out in an aqueous medium containing 100% water or water mixed with a small amount of an organic solvent. The pH is maintained in the range of from about 2.5 to about 6.5 with an organic or inorganic acidic or basic substance, preferably with a buffer solution of dipotassium hydrogen phosphate/phosphoric acid. The temperature for conducting the rearrangement reaction is preferably in the range from about 60° C. to about 200° C., more preferably from about 80° C. and 140° C. In one preferred embodiment, the mixture of cyclopentenones of Formulae 3 and 1, generated from the rearrangement reaction, is directly subjected to Step (c) without further purification. Step (c) is an isomerization reaction, which can be conducted in the presence of chloral hydrate and triethylamine. By the isomerization reaction, the cyclopentenones of Formula 3 are isomerized into the cyclopentenones of Formula 1. The resultant crude Cyclopentenones of Formula 1 are racemic.

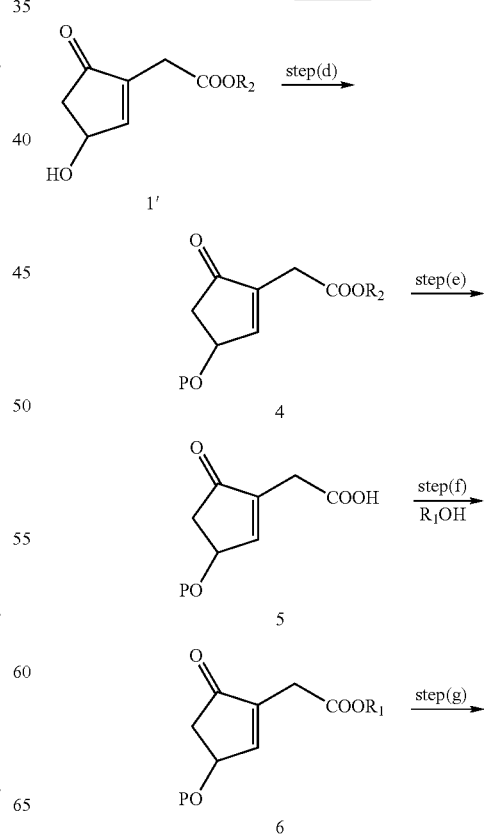

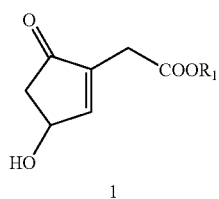

The reaction in Step (d) of Scheme B is a protective reaction. Preferred protective groups are base stable, and include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_aR_bR_c$ wherein $R_a$, $R_b$ and $R_c$ are each independently a $C_{1-4}$ alkyl, phenyl, benzyl, a substituted phenyl, or a substituted benzyl. The reaction conditions for conducting the protection are well known in the art. Examples of suitable protective groups are described by T. W. Greene in "Protective Groups in Organic Synthesis," John Wiley & Sons, Inc., 1981. For example, Cyclopentenones of Formula 1' are dissolved in dichloromethane and p-toluenesulfonic acid in a catalytic amount is added thereto. The reaction mixture is subjected to an ice bath, and an appropriate amount of 3,4-dihydro-2H-pyran is added, and then is stirred at room temperature for about 10 minutes to about 10 hours to obtain the protected Cyclopentenones of Formula 4.

The reaction in Step (e) of Scheme B is a hydrolysis reaction that is conducted in the presence of an enzyme, preferably a *Candida antarcitica* lipase, in an aqueous phase (water or buffer), and/or an organic solvent. The reaction in Step (f) of Scheme B is an esterification reaction on the carboxyl group of the hydrolyzed Cyclopentenones with an alcohol of formula $R_1OH$ in the presence of a condensation reagent that is used for activating the carboxyl group or the alcohol moiety, and a base. Examples of The condensation reagent include, but are not limited to, 1,3-dicyclohexylcarbodiimide, chloride, 2-chloro-1-methyl-pyridium iodide, 2-chloro-4,5-dihydro-1,3-dimethyl-1H-imidazolium chloride, N,N-diphenylchlorophenylmethyleniminium chloride, and the like, and examples of the base include pyridine, triethylamine, diisopropylethylamine, N,N-dimethylaminopyridine, and the like, in an appropriate solvent, including dichloromethane, tetrahydrofuran, and 1,2-dichloroethane, and a mixture thereof.

The reaction in Step (g) of Scheme B is a deprotection reaction, which can be conducted in a conventional manner. For instance, the Cyclopentenone of Formula 6 wherein $R_1$ is 2-naphthyl, and P is a tetrahydropyranyl protective group is dissolved in a suitable solvent such as methanol, treated with a suitable deprotective agent such as hydrogen chloride, p-toluenesulfonic acid, or pyridinium p-toluenesulfonate, and stirred at room temperature for 10 minutes to 10 hours to obtain the deprotected products of formula I.

II-2. Enantioselective (R)-Esterification of Racemic Alcohols (R)-1

As shown in Scheme C, racemic cyclopentenones of Formula 1 are reacted with an acyl donor of Formula A,

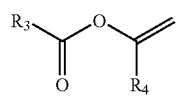

wherein $R_3$ and $R_4$ are independently a lower alkyl, in the presence of an enantioselective lipase, wherein the acyl donor preferentially reacts with the Cyclopentenones in (R)-form, thereby generating a mixture consisting of the optically active esters of Formula (R)-7 and the unreacted alcohols of Formula (S)-1 (Scheme C).

Scheme C

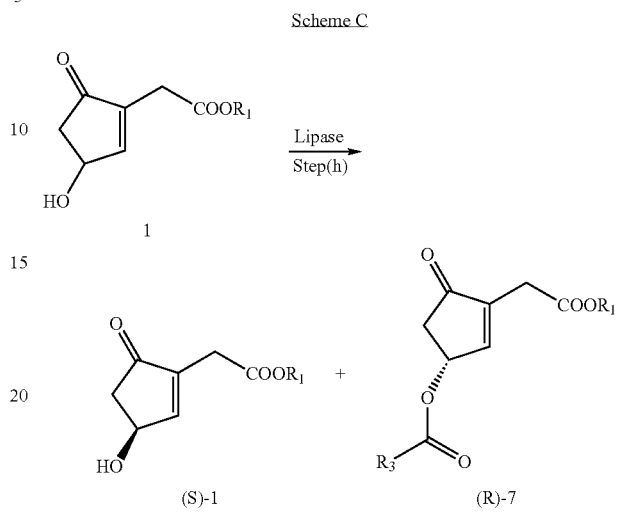

According to the invention, the resultant esters of Formula (R)-7 possess an optical activity of at least 85% e.e., preferably at least 90% e.e., most preferably at least 95% e.e and up to 99% e.e. Moreover, according to a preferred embodiment of the present invention, in Formula 1, $R_1$ is $C_1$-$C_{15}$ alkyl, benzyl, naphthyl, or phenyl, each of which is unsubstituted or substituted, and more preferably, is selected from methyl, ethyl, benzyl, naphthyl or trichloroethyl.

In one embodiment, the enantioselective lipase used in the invention is derived from a pig liver, a porcine pancrease, or microorganisms, e.g., *Achromobacter* spp., *Alcaligenes* spp., *Aspergillus niger, Candida antarcitica, Candida rugosa, Candida lypolytica, Chromobacterium viscosum, Mucor janvanicus, Mucor miehei, Penicillum Camenberti, Penicillium roqueforteii, Pseudomonas cepacia, Pseudomonas fluorescence, Pseudomonas* spp., *Pseudomonas stutzuri, Rhizopus Delmar, Rhizopus Niveus, Rhizopus oryze,* and *Rhizopus* spp. More preferably, the steroselective lipase is derived from *Candida antarcitica, Achromobacter* spp., *Alcaligenese* spp., *Pseudomonas fluorescens, Pseudomonas stutzri,* or *Pseudomonas cepacia.*

The lipase may be present in the process of the invention in any form, including a purified form, or a crude form, or a natural form associated with the microorganism per se from which the lipase is derived, as long as its optical selectivity in the esterification is maintained. The chemical stability, activity, or enantioselectivity of the lipase can be further enhanced by gene modification, DNA recombination, or immobilization. In preferred embodiments, the lipase is a *Pseudomonas* lipase named "AK" or "PS," which is commercially available from the Amano Pharmaceutical Company, or the lipase derived from *Achromobacter* spp., or the lipase derived from *Alcaligenese* spp., or lipase named "Lipolase" or "Novozyme" commercially available from Novo Nordisk.

The enantioselective esterification may be performed in a single organic solvent or a mixture of organic solvents, which is selected from hexane, cyclohexane, toluene, tetrahydrofuran, methyl ethyl ketone, methyl isobutyl ketone, ether, isopropyl ether, methyl isopropyl ether, and tert-butyl methyl ether and the mixtures thereof. The amount of the lipase used varies with many factors such as the activity of the lipase, the amount of the substrates, or the solvents used. In one embodiment of the present invention, the lipase is used in an amount ranging from 0.01 mass equivalent to 10 mass equivalents per mass equivalent of the cyclopentenone of Formula 1.

The reaction mixture should be constantly stirred, shaked, or ultrasounded to ensure a good contact between the reactants and the lipase. Further, the temperature suitable for the reaction is between 5° C. and 50° C., preferably at ambient temperature. In addition, the enantiomerically selective esterification may be stopped when an appropriate conversion of the starting material is obtained by removing the lipase from the reaction mixture. In one embodiment, the lipase is removed to stop the enzymatic esterification when a conversion rate of between 30% to 70%, more preferably of approximately 50% is achieved. In one embodiment, the acyl donor used in the invention comprises vinyl acetate, isopropenyl acetate, vinyl valerate, isopropenyl valerate, vinyl butyrate, or isopropenyl butyrate or a mixture thereof.

II-3 Removal of the untreated (S)-alcohols

The removal of the untreated (S)-alcohols comprises direct separation of the ester of Formula (R)-7 and the unreacted alcohol (S)-1 in the reaction mixture from step (h). Since the structures and the properties of the esters of Formula (R)-7 are distinctively different from those of the alcohols of Formula (S)-1, the esters of Formula (R)-7 can be easily isolated from the mixture by a conventional method, such as flash chromatography on silica gel:

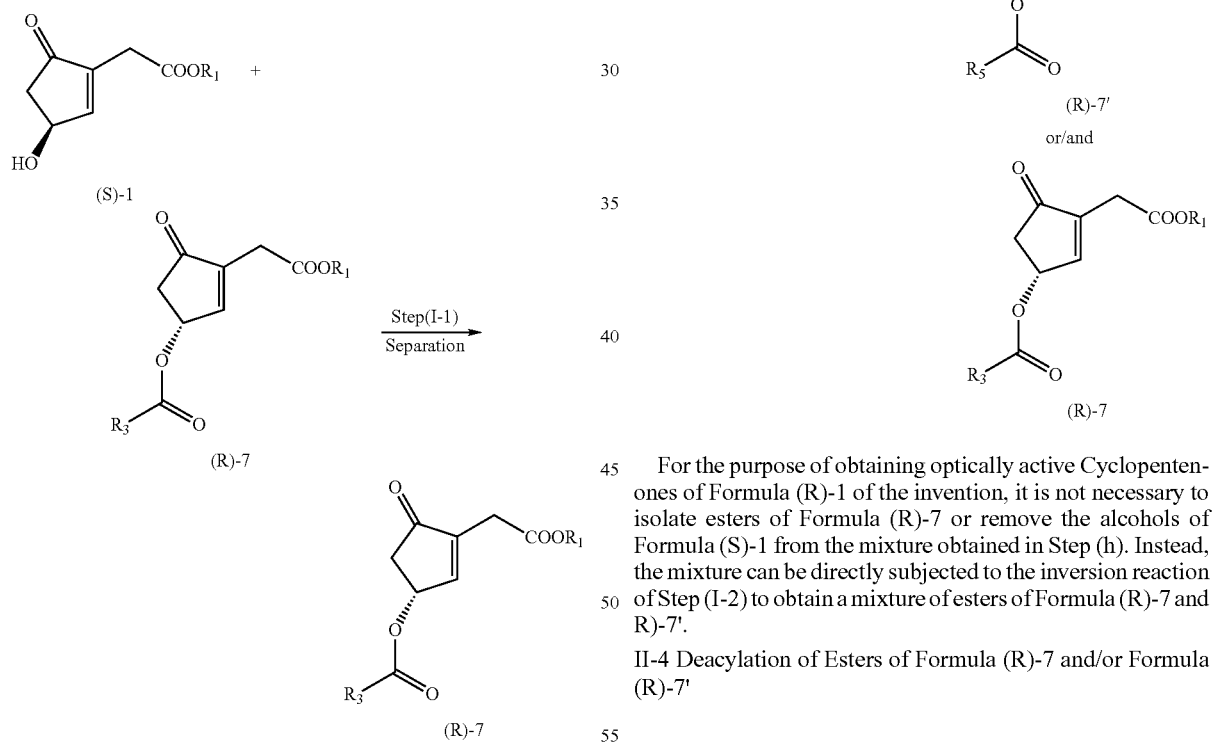

Alternatively, according to one embodiment of the present invention, the unreacted alcohols (S)-1 are converted into esters of Formula (R)-7 or (R)-7', by conversion of the OH group into an acyloxy group with an acyloxy donor of Formula $R_5COOH$, wherein $R_5$ is as defined for $R_1$ or is $R_3$, in the presence of a dialkylazodicarboxylate and triarylphosphine in a suitable solvent. Preferably, the dialkylazodicarboxylate is diethylazodicarboxylate, diisopropylazodicarboxylate, or dibenzylazodicarboxylate, and/or the triarylphosphine is triphenylphosphine, and/or the solvent is toluene, and/or the acyloxy donor is a carboxylic acid and/or the $R_5$ is a lower alkyl or $R_3$. In Step (I-2), almost 100% of the alcohols of Formula (S)-1 in the mixture are converted to the esters of Formula (R)-7'.

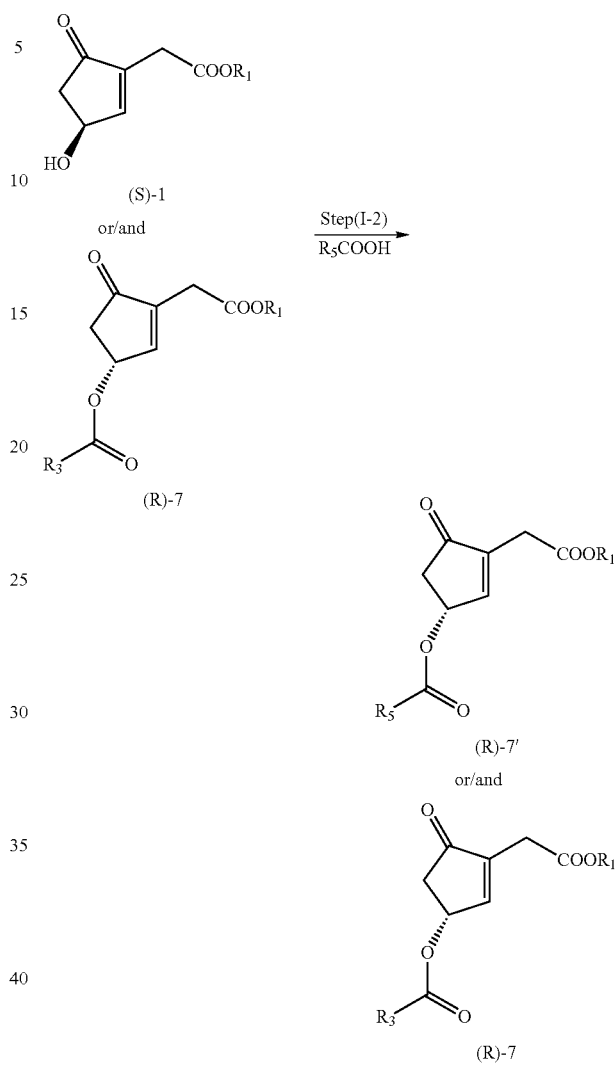

For the purpose of obtaining optically active Cyclopentenones of Formula (R)-1 of the invention, it is not necessary to isolate esters of Formula (R)-7 or remove the alcohols of Formula (S)-1 from the mixture obtained in Step (h). Instead, the mixture can be directly subjected to the inversion reaction of Step (I-2) to obtain a mixture of esters of Formula (R)-7 and R)-7'.

II-4 Deacylation of Esters of Formula (R)-7 and/or Formula (R)-7'

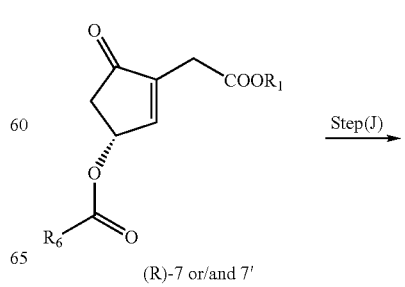

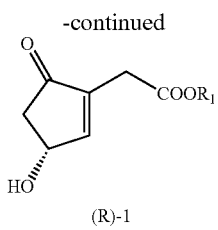

(R)-1

$R_6 = R_3$ or/and $R_5$

According to the invention, Step (J) is a deacylation reaction. In one embodiment of the invention, the deacylation reaction is a chemical hydrolysis or an alcoholysis performed in the presence of an alcohol and an acid catalyst, such as phosphoric acid, p-toluenesulfonic acid, hydrobromic acid, hydrochloric acid, nitric acid or sulfuric acid or a mixture thereof, for cleavaging esters of (R)-7 and/or (R)-7' to obtain Cyclopentenones of Formula (R)-1. Preferably, the acid is sulfuric acid and the alcohol is $R_1OH$, wherein $R_1$ is as defined above.

In another embodiment of the invention, the deacylation reaction in Step (J) is an enzymatic cleavage reaction. The enzymatic cleavage reaction is either a hydrolysis or an alcoholysis and can be performed in the presence of water, buffer, water- or buffer-saturated organic solvent(s), an alkyl or aryl alcohol, or an alcohol containing aqueous or non-aqueous system. In addition, the reaction system for the enzymatic deacylation can be a homogenous or two-phase system containing water or buffer and a water-insoluble solvent or solvents. The esters should be either dissolved or finely dispersed in the reaction system to provide a good contact with the lipase therein. If necessary, a phase transfer catalyst, e.g., a salt or a surfactant, can be added to the system to increase the reaction rate. The organic solvents can be immiscible with water or should be saturated with water or buffer, or water-soluble organic solvents, such as alcohols. Suitable buffers include, but are not limited to, those prepared from a halide, a carbonate, a phosphate, a sulfate, a nitrate, a bicarbonate, and/or an acetate and are preferably at a pH ranging from 5 to 8. Suitable organic solvents used in the reaction can be water-miscible solvents, which include but are not limited to, alkyl alcohols, aryl alcohols, alkenyl alcohols, methyl sulfoxide, acetone, dimethyl formamide, acetonitrile, and a mixture thereof, or water-immiscible solvents, which include but are not limited to, hexane, toluene, ether, petroleum ether, isopropyl ether, methyl tert-butyl ether, tetrahydrofuran, methyl ethyl ketone, methyl isobutyl ketone, dioxane, and a mixture thereof.

The enzyme employed is a lipase suitable for the hydrolysis or alcoholysis of the ester. Preferably, the lipase used in Step (J) is derived from *Candida antarcitica, Achromobacter* spp., *Alcaligenese* spp., *Pseudomonas fluorescens, Pseudomonas stutzri*, or *Pseudomonas cepacia*. More preferably, the lipase is derived from *Candida antarcitica, Psudomonas* spp., or *Achromobacter* spp., and most preferably from *Candida antarcitica*.

The reaction is monitored by HPLC using a chiral column and stopped by removing the lipase, preferably when the optical purity of the product decreases to about 95% e.e. Optionally, the unreacted esters of (R)-7 and/or (R)-7' can be removed after the deacylation. According to the invention, alcohols of Formula (R)-1 are produced with an optical activity of at least 95% e.e., preferably at least 98% e.e.

II-5 Transesterification of the Optically Active Cyclopentenones of Formula (R)-1

In one embodiment of the invention, Cyclopentenones of Formula (R)-1 are subjected to a transesterification reaction such that the $R_1$ in the cyclopentenones is replaced with another substituent. The transesterification of the optically active Cyclopentenones of Formula (R)-1 according to the invention is conducted in the same manner as shown in Section II-1 (Scheme B) except that the starting material is the optically active Cyclopentenone instead of the racemic material. In the transesterification, the optical purity of the substrate remains unchanged.

III. Second Aspect of the Invention

The present invention further provides a compound of Formula 1A

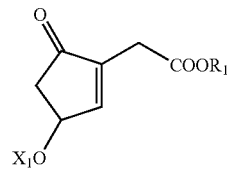

1A wherein $X_1$ is H or a protective group for the hydroxy group; and $R_1$ is an alkyl, an alkenyl, an alkynyl, an aryl, or an aralkyl, each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl and pyrrolidinonyl, or a protective group for the carboxyl group, with the proviso that $R_1$ is not a straight, unsubstituted alkyl.

According to one embodiment, the compound of Formula 1A is enriched in the R configuration and has an optical purity of at least 95% enantiomeric excess.

Particularly, the invention provides a compound of Formula 1A in which $R_1$ is a branched alkyl, an alkenyl or an alkynyl, each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl and pyrrolidinonyl, or a protective group for the carboxyl group, and preferably $R_1$ is an aralkyl which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl, and preferably said aralkyl is benzyl which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl; or an aryl which is unsubstituted or substituted with one or more substituents selected from the group consisting of halogen, alkyl, alkoxyl, thioalkoxyl, alkoxycarbonyl, carbonyl and cyano; and preferably said aryl is selected from the group consisting of phenyl, naphthyl, pyrenyl and phenanthrenyl each of which is unsubstituted or substituted with one or more substituents selected from the group consisting of halogen, alkyl, alkoxyl, thioalkoxyl, alkoxycarbonyl, carbonyl and cyano.

More particularly, the invention provides a compound of Formula 1A in which $R_1$ is naphthyl, benzyl, 2-cyanoethyl, menthyl, methoxybenzyl, piperonyl, phenyl, alkoxycarbonylphenyl, trichloroethyl. or diphenylmethyl.

The present invention will be further described in the following examples. However, the examples will not make any limitations to the scope of the invention. Any modifications or alterations on the invention that can be easily accomplished by persons having ordinary skill in the art are encompassed in the disclosure of the specification and the accompanying claims.

EXAMPLES

Example 1

2-Ethoxycarbonylmethyl-4-hydroxy-2-cyclopenten-1-one

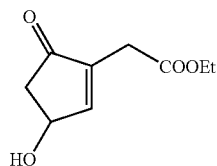 [SMILES: CCOC(=O)CC1=CC(O)CC1=O]

The example was conducted according to the procedure shown in Scheme B.

Step (a):

A reaction flask (2-litter) was flame dried under vacuum and set under nitrogen. 400 ml of anhydrous THF, 59.68 g of diisopropylamine, and about 352 ml of 1.6 M n-butyl lithium in hexane were introduced into the reaction flask and stirred under a temperature ranging from −20° C. to 0° C. for about one hour. Subsequently, the reaction temperature was lowered to about −70° C. using a dry ice/acetone bath. A solution of ethyl acetate (47.2 g) diluted in 100 ml THF was added with a dropping funnel to the reaction mixture. 51.5 g of furfural was then added to the reaction mixture, and upon completion of the reaction, the reaction mixture was quenched by a saturated aqueous solution of ammonium chloride and then stirred for one hour. Upon completion, the phases were separated and the aqueous phase was extracted twice with ethyl acetate (2×500 ml). The organic layers were combined and washed with brine (500 ml), dried over anhydrous magnesium sulfate, filtered, and concentrated under vacuum (40° C., 2 mmHg). Dark yellowish to brownish oil (about 120 g) was obtained.

Step (b):

The product obtained from step (a) was used in Step (b) without further purification. In a three-necked flask equipped with a stirrer and a condenser, the product from step (a), water (4800 g), and dipotassium hydrogen phosphate (5.1 g) were charged and stirred. The pH of the reaction solution was adjusted to about 3 using phosphoric acid. The reaction mixture was refluxed at a temperature around or higher than 100° C. under a nitrogen stream. When the reflux reaction was completed, the reaction mixture was cooled and extracted using ethyl acetate until the aqueous phase did not contain the desired product. The ethyl acetate was evaporated off from the extracted product to give a mixture containing 2-ethoxycarbonylmethyl-4-hydroxy-2-cyclopen-1-one and 2-ethoxycarbonylmethyl-3-hydroxy-4-cyclopean-1-one (about 120 g in total).

Step (c):

To the reaction mixture (about 120 g) obtained from step (b), 6 g of triethylamine, 0.6 g of chloral monohydrate, and 250 ml of toluene were added. The mixture was stirred at room temperature for 1 to 24 hours until 2-ethoxycarbonylmethyl-3-hydroxy-4-cyclopenten-1-one was completely converted into 2-ethoxycarbonyl-methyl-4-hydroxy-2-cyclopenten-1-one, wherein the conversion was monitored by a thin layer chromatography (TLC). The reaction mixture was further concentrated to obtain a dark brownish oily product, which was subsequently subjected to a flash chromatography, wherein the column was packed with silica gel and eluted with a solvent mixture containing hexane and ethyl acetate in different ratios. Finally, the titled compound, 2-ethoxycarbonylmethyl-4-hydorxy-2-cyclopen-1-one (about 57 g) was obtained in a pure form. $^1$H-NMR (CDCl$_3$/TMS): δ 7.44 (s,1H), 4.98 (m, 1H), 4.16 (q, 2H), 3.25 (s,2H), 3.11 (br, 1H), 2.83 (dd, 1H), 2.34 (dd, 1H),1.27 (t, 3H).

Example 2

2-Methoxycarbonylmethyl-4-hydroxy-2-cyclopenen-1-one

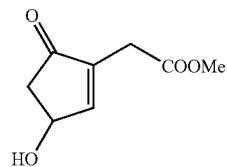 [SMILES: COC(=O)CC1=CC(O)CC1=O]

The procedure of Example 1 was repeated except that methyl acetate (40 g) was used instead of ethyl acetate. The titled compound was obtained in the form of dark oil (24 g). $^1$H-NMR (CDCl$_3$/TMS): δ 7.45 (s,1H), 5.01 (m, 1H), 3.72 (s, 3H), 3.28 (s,2H), 2.85 (dd, 1H), 2.35 (dd, 1H), 1.67 (brs, 1H).

Example 3

2-Benzoxycarbonylmethyl-4-hydroxy-2-cyclopenten-1-one

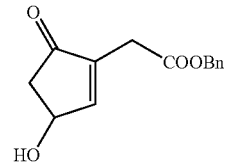

The procedure of Example 1 was repeated except that benzyl acetate (80.8 g) was used instead of ethyl acetate. The titled compound was obtained in the form of dark oil (55 g).

¹H-NMR (CDCl₃/TMS): δ 7.15~7.55 (m, 6H), 5.17 (s, 2H), 5.01 (m, 1H), 3.31 (s,2H), 2.83 (dd, 1H), 2.33 (m, 1H).

Example 4

2-Ethoxycarbonylmethyl-4-tetrahydropyranyloxy-2-cyclopenten-1-one

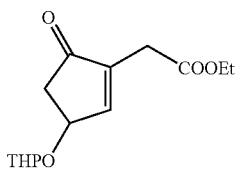

100 g of 2-ethoxycarbonylmethyl-4-hydroxy-2-cyclopenten-1-one was dissolved in 1000 ml dichloromethane, and added with 55 g of 3,4-dihydro-2H-pyran and 2 g of p-toluenesulfonic acid monohydrate, and then stirred at room temperature for about 3 hours. Upon completion of the reaction, the reaction mixture was washed with 400 ml of a saturated aqueous sodium bicarbonate solution, dried over anhydrous magnesium sulfate, and concentrated to obtain 2-ethoxycarbonylmethyl-4-tetrahydropyranyloxy-2-cyclopenten-1-one (138.5 g). ¹H-NMR (CDCl₃/TMS): δ 7.40-7.68 (m, 1H), 4.70~5.02 (m, 2H), 4.15 (q, 2H), 3.88 (m, 1H), 3.54 (m,1H), 3.23 (q, 2H), 2.79 (m,1H), 2.37 (m, 1H), 1.77 (m, 2H), 1.55 (m, 4H), 1.25 (t, 3H).

Example 5

2-Hydroxycarbonylmethyl-4-tetrahydropyranyloxy-2-cyclopenten-1-one

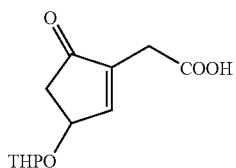

50 g of 2-ethoxycarbonylmethyl-4-tetrahydropyranyloxy-2-cyclopenten-1-one obtained from Example 4 and 5 g of *Candida antarcitica* lipase were suspended in 500 ml of phosphate buffer (10 mM, pH 6.5-7.5) and stirred at room temperature. The pH of the solution was maintained by 1N sodium hydroxide solution and finally adjusted to 8.0 upon completion of the reaction. The reaction mixture was washed with 300 ml ethyl acetate twice. The pH of the aqueous layer was further adjusted to 3.0 using saturated sodium hydrogensulfate solution. The aqueous layer was washed twice again using 300 ml ethyl acetate. The organic layers were combined and dried over anhydrous magnesium sulfate, filtered, and concentrated to obtain 2-hydroxycarbonylmethyl-4-tetrahydropyranyloxy-2-cyclopen-1-one (31.5 g, 75% yield). ¹H-NMR (CDCl₃/TMS): δ 7.45~7.61 (m, 1H), 4.73~5.02 (m, 2H), 3,88 (m, 1H), 3.55 (m,1H), 3.31 (m, 2H), 2.82 (m,1H), 2.38 (m, 1H), 1.42~1.88 (m, 6H).

Example 6

2-(1,1,1-Trichloroethoxycarbonylmethyl)-4-hydroxy-2-cyclopenten-1-one

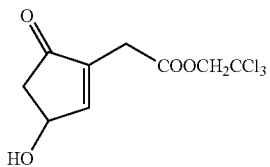

5 g of 2-hydroxycarbonylmethyl-4-tetrahydropyranyloxy-2-cyclopen-1-one obtained from Example 5, 2,2,2-trichloroethanol (4.7 g), dichloromethane (50 ml), and 0.2 g 4-dimethylaminopyridine (DMAP) were added together to a 30 ml dichloromethane solution containing 1,3-dicyclohexylcarbodiimide (7 g). The reaction mixture was stirred at room temperature for about 4 hours. The precipitate was filtered off. The filtrate was washed with 20 ml of diluted hydrochloride solution, water, dried over anhydrous magnesium sulfate, filtered, and evaporated under vacuum. The crude product was dissolved in 30 ml acetone and 6 ml water, further added with 3 ml 3N HCl(aq) and stirred overnight. Upon completion of the reaction, acetone was evaporated and the reaction mixture was diluted with ethyl acetate and washed with an aqueous sodium bicarbonate solution and a brine solution. The organic liquid was subjected to the previous work-up procedure, including dehydration, filtration, and evaporation, and purification by chromatography on silica gel to obtain the titled compound (4.8 g, 80%). ¹H-NMR (CDCl₃/TMS): δ7.49 (m, 1H), 5.02 (m, 1H), 4.75 (s, 2H), 3.42 (s, 2H), 2.86 (dd, 1H), 2.35 (dd, 1H), 1.78 (brs, 1H).

Example 7

2-(2-Naphthyloxycarbonylmethyl)-4-hydroxy-2-cyclopenten-1-one

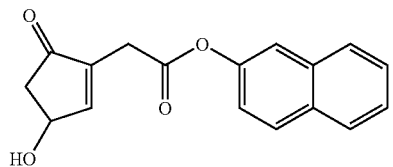 [SMILES: O=C(CC1=CC(O)CC1=O)Oc1ccc2ccccc2c1]

5 g of 2-Hydroxycarbonylmethyl-4-tetrahydropyranyloxy-2-cyclopenten-1-one (21 mmol) obtained from Example 5, 2-naphthol (4.7 g, 32 mmol), dichloromethane (50 ml), and 0.2 g 4-(dimethylamine)pyridine were added together to a 50 ml dichloromethane solution containing 1,3-dicyclohexylcarbodiimide (7 g, 34 mmol). The reaction mixture was stirred at room temperature for about 4 hours. The precipitate was filtered off. The filtrate was washed with 20 ml of diluted hydrochloride solution, water, dried over anhydrous magnesium sulfate, filtered, and evaporated under vacuum. The crude product was dissolved in 30 ml acetone and 6 ml water, further added with 0.3 g p-toluenesulfonic acid and stirred overnight. Upon completion of the reaction, acetone was evaporated and the reaction mixture was diluted with ethyl acetate and washed with an aqueous sodium bicarbonate solution and a brine solution. The organic liquid was subjected to the previous work-up procedure, including dehydration, filtration, and evaporation, and purification by chromatography on silica gel to obtain the title compound as white solid. MP: 81° C. (4.2 g, 71%) $^1$H-NMR (CDCl$_3$/TMS): δ 7.82 (m,2H), 7.78 (d, 1H), 7.55 (m,2H), 7.46 (m,2H), 7.21 (dd, 1H), 5.04 (m, 1H), 3.56 (s, 2H), 2.89 (dd, 1H), 2.38 (dd, 1H), 1.60 (brs, 1H).

Example 8

A mixture of (R)-2-benzoxycarbonylmethyl-4-acetyloxy-2-cyclopenten-1-one and (S)-2-benzoxycarbonylmethyl-4-hydroxy-2-cyclopenten-1-one

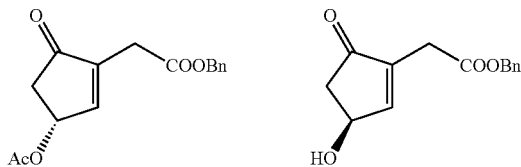

10 g of racemic 2-benzoxycarbonylmethyl-4-hydroxy-2-cyclopenten-1-one obtained from Example 3, 10 ml of vinyl acetate, 1 g of lipase derived from *Pseudomonas cepacia,* and 100 ml of methyl isobutyl ketone (hereinafter referred to as "MIBK") were added to a 250 ml reaction flask and stirred at a temperature from 0° C. to 50° C. When about 45% to 55% of the esterification reaction was achieved, the reaction was stopped by removal of the lipase. The reaction mixture was concentrated under vacuum evaporation (50° C., 20 mmHg) and the product as a dark brown oil was formed, which contained the (R)-ester, i.e., (R)-2-benzoxy carbonyl methyl-4-acetyloxy-2-cyclopenten-1-one and the unreacted (S)-alcohol, i.e., (S)-2-benzoxycarbonylmethyl-4-hydroxy-2-cyclopenten-1-one. Optionally, the (R)-ester (4.8 g, 99% ee) and the unreacted (S)-alcohol (4.2 g, 99% ee) were separated by a flash column.

Examples 9 to 26

Examples 9 to 26 were conducted in the same manner as described in Example 8 except that the acyl donors, solvents, and lipase types used were different. The results are shown in Table 1.

TABLE 1

Details of Examples 9 to 26

| Example No. | substrate R$_1$ | acyl donor | solvent | lipase type | (R)-ester yield | (R)-ester optical purity (% e.e.) | (S)-alcohol yield | (S)-alcohol optical purity (% e.e.) |
|---|---|---|---|---|---|---|---|---|
| 9 | methyl | isopropenyl acetate | MIBK | *Pseudomonas fluorescens* | 35% | 95 | 43% | 89 |
| 10 | methyl | vinyl acetate | — | *Candida antarctica* | 36% | 92 | 48% | 82 |
| 11 | ethyl | isopropenyl acetate | toluene | *Candida antarctica* | 30% | 85 | 45% | 78 |
| 12 | ethyl | vinyl acetate | MIBK | *Pseudomonas fluorescens* | 42% | 98 | 44% | 94 |
| 13 | ethyl | vinyl acetate | IPE | *Mucor miehei* | 32% | 86 | 42% | 80 |
| 14 | benzyl | vinyl acetate | MTBE | *Pseudomonas fluorescens* | 37% | 93 | 45% | 94 |
| 15 | benzyl | vinyl acetate | IPE | *Pseudomonas cepacia* | 40% | 99 | 42% | 98 |
| 16 | benzyl | vinyl acetate | MIBK | *Alcaligenese* spp. | 41% | 97 | 45% | 94 |
| 17 | benzyl | vinyl acetate | toluene | *Achromobacter* spp. | 37% | 92 | 38% | 88 |
| 18 | 2-naphthyl | vinyl acetate | MIBK | *Pseudomonas cepacia* | 42% | 98 | 39% | 99 |
| 19 | 2-naphthyl | vinyl acetate | MIBK | *Pseudomonas fluorescens* | 45% | 90 | 36% | 98 |
| 20 | 2-naphthyl | vinyl acetate | MIBK | *Candida antarctica* | 36% | 75 | 37% | 89 |
| 21 | 2-naphthyl | vinyl acetate | MIBK | *Alcaligenese* spp. | 41% | 98 | 35% | 99 |

TABLE 1-continued

Details of Examples 9 to 26

(R)-ester (S)-alcohol

| Example No. | substrate $R_1$ | acyl donor | solvent | lipase type | (R)-ester yield | (R)-ester optical purity (% e.e.) | (S)-alcohol yield | (S)-alcohol optical purity (% e.e.) |
|---|---|---|---|---|---|---|---|---|
| 22 | 2-naphthyl | vinyl acetate | MIBK | *Pseudomonas stutzri* | 36% | 90 | 28% | 98 |
| 23 | 1,1,1-trichloro-ethyl | vinyl acetate | MIBK | *Pseudomonas cepacia* | 38% | 98 | 42% | 98 |
| 24 | 1,1,1-trichloro-ethyl | vinyl acetate | MIBK | *Pseudomonas fluorescens* | 36% | 95 | 41% | 98 |
| 25 | 1,1,1-trichloro-ethyl | vinyl acetate | MIBK | *Candida antarcitica* | 36% | 92 | 31% | 96 |
| 26 | 1,1,1-trichloro-ethyl | vinyl acetate | MIBK | *Alcaligenese* spp. | 34% | 97 | 37% | 99 |

The symbol "—" means that no solvents or diluents were added.
The abbreviation "MIBK" refers to methyl isobutyl ketone.
The abbreviation "IPE" refers to isopropyl ether.

Examples 27 and 28

2-Benzoxycarbonylmethyl-4-acetyloxy-2-cyclopenten-1-one

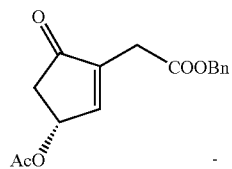

Examples 27

The unreacted (S)-alcohol, i.e., (S)-2-Benzoxy carbonylmethyl-4-hydroxy-2-cyclopen-1-one (4.2 g, 98% e.e.) obtained from Example 8, acetic acid (1.54 g, 1.5 mol. Eq.), and triphenylphosphine (6.74 g, 1.5 mol. Eq.) were dissolved together in toluene in a closed reaction flask. Subsequently, the reaction mixture was cooled to a temperature of about 0 to 10° C. and then slowly added with diisopropylazodicarboxylate (DIAD) (4.5 g, 1.3 mol. Eq.). The temperature was maintained at 0 to 10° C. until the reaction was completed and then the reaction mixture was brought to room temperature. The resultant precipitate was filtered and the filtrate was evaporated under vacuum to remove toluene. The crude product, i.e., (R)-2-benzoxycarbonylmethyl-4-acetyloxy-2-cyclopenten-1-one (5.4 g, 98% e.e.), was obtained. $^1$H-NMR (CDCl$_3$/TMS): δ 7.43 (m, 1H), 7.33 (m, 5H), 5.78 (m, 1H), 5.13 (s, 2H), 3.31 (s, 2H), 2.87 (dd, 1H), 2.37 (dd, 1H), 2.06 (s, 3H).

Example 28

A mixture (5.75 g) containing the (R)-ester: 2-benzoxycarbonylmethyl-4-acetyloxy-2-cyclopen-1-one and the unreacted (S)-alcohol: 2-benzoxycarbonylmethyl-4-hydroxy-2-cyclopenten-1-one obtained from Example 15 was combined with toluene (50 ml), acetic acid (1.06 g, 1.5 mol. eq.), and triphenylphosphine (4.6 g, 1.5 mol. eq.). The reaction mixture was stirred at room temperatures until a homogeneous reaction mixture was formed. The reaction mixture was cooled and gradually added with diisopropylazocarboxylate (approx. 3.1 g, 1.3 mol. eq.). After the reaction was completed, the reaction mixture was heated to ambient temperature and stirred for one day. The resultant precipitate was filtered and the filtrate was evaporated under vacuum to remove toluene. The crude product (9.7 g) containing the (R)-ester, residues, and by-products from the Mitsunobu reaction was obtained. The crude product was directly used in the following reactions or slightly purified by a flash column. The titled compound (about 4.8 g) was obtained with optical purity of about 99% e.e.

Example 29

(R)-2-ethoxycarbonylmethyl-4-acetyloxy-2-cyclopenten-1-one

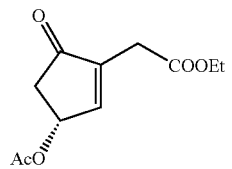 [SMILES: CCOC(=O)CC1=C[C@H](OC(C)=O)CC1=O]

A mixture containing the (R)-ester: 2-ethoxycarbonylmethyl-4-acetyloxy-2-cyclopenten-1-one and the (S)-alcohol: 2-ethoxycarbonylmethyl-4-hydroxy-2-cyclopenten-1-one was subjected to the procedure as described in Example 28 to obtain the titled compound (7.2 g).

$^1$H-NMR (CDCl$_3$/TMS): δ 7.44 (s, 1H), 5.79 (d, 1H), 4.15 (q, 2H), 3.25 (s, 2H), 2.88 (dd, 1H), 2.37 (dd, 1H), 2.07 (s, 3H), 1.25 (s, 3H).

Example 30

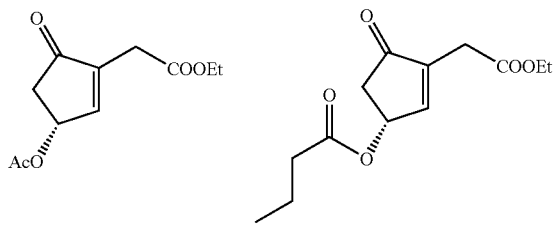 [SMILES: CCOC(=O)CC1=C[C@H](OC(C)=O)CC1=O ; CCCC(=O)O[C@H]1C=C(CC(=O)OCC)C(=O)C1]

Example 29 was conducted according to the procedure of Example 28 except the butyric acid was used in the reaction instead of acetic acid. The titled mixture was obtained as a dark oil (yield: about 90%)

Examples 31 to 33

(R)-2-ethoxycarbonylmethyl-4-hydroxy-2-cyclopenten-1-one

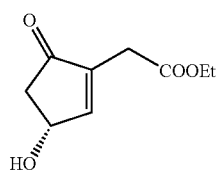 [SMILES: CCOC(=O)CC1=C[C@H](O)CC1=O]

Examples 31: 5 g of (R)-2-ethoxycarbonylmethyl-4-acetyloxy-2-cyclopenten-1-one (96% e.e.) was dissolved in 40 ml ethanol. 5 g of sulfuric acid was gradually added to the reaction mixture that was then stirred at 40° C. for 4 to 5 hours. The reaction mixture was poured into an iced water and the pH of the solution was adjusted to about 4 to 6 using a saturated aqueous sodium bicarbonate solution. The reaction mixture was concentrated under vacuum to evaporate off ethanol, further diluted with 300 ml ethyl acetate for extraction, and stood to allow phase separation. The aqueous layer was washed twice with about 100 ml ethyl acetate. The organic solutions were collected, combined, and washed with a saturated sodium bicarbonate solution as well as a brine solution, respectively. The reaction mixture was dried with anhydrous magnesium sulfate and concentrated under vacuum. The residue was purified by flash chromatography on silica gel to give the titled compound as an oil (4.1 g, 96% e.e.).

Examples 32: 5 g of (R)-2-ethoxycarbonylmethyl-4-acetyloxy-2-cyclopenten-1-one (96% e.e.) added with 50 ml of MIBK, 5 g of ethanol, and 0.5 g of Candida antarcitica Lipase (obtained from Novo Industry) were stirred together in a reaction flask under room temperature. The reaction was monitored by HPLC and stopped until the optical purity of the reaction substrate decreased to 99% e.e. by filtering off the lipase. The reaction mixture was concentrated to remove the solvents and was further subjected to a short column to remove the unreacted ester to obtain the titled compound having a high optical purity (4.2 g, 99% e.e.).

Examples 33: Example 33 was conducted according to the procedure of Example 32 except the lipase derived from Achromobacter was used instead of Candida antarcitica Lipase. The titled compound was obtained with high optical purity (4.1 g, 99% e.e.).

Examples 34 and 35

(R)-2-benzoxycarbonylmethyl-4-hydroxy-2-cyclopenten-1-one

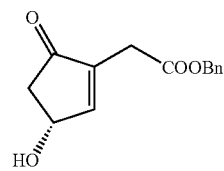

Example 34: Example 34 was conducted according the procedure of Example 32 except that the starting material was (R)-2-benzoxycarbonylmethyl-4-acetyloxy-2-cyclopenten-1-one (4 g, 97% e.e.) and benzyl alcohol were used instead of (R)-2-ethoxycarbonylmethyl-4-acetoxy-2-cyclopenten-1-one and ethanol. The titled compound was obtained with high optical purity (3.4 g, 99% e.e.).

Example 35

Examples 34: 5 g of (R)-2-benzoxycarbonylmethyl-4-acetyloxy-2-cyclopenten-1-one (5 g, 98% e.e.), 0.5 g of Candida antarcitica lipase, and 50 ml of phosphate buffer (10 mM, pH 7) were added together and stirred at room temperatures. The pH of the reaction mixture was maintained at about 6.5 to 7.5 with 0.1N sodium hydroxide solution. After about 3 to 4 hours, the reaction was stopped by filtering off the lipase. The product was extracted from the aqueous phase twice with ethyl acetate (50 ml). Subsequently, the collected organic layer was washed with a saturated sodium bicarbonate solution and a brine solution, respectively, dried over anhydrous magnesium sulfate, and evaporated under vacuum. The residue was purified by flash chromatography on silica gel to give the titled compound as an oil (3.2 g, 98% e.e.).

Example 36

(R)-2-ethoxycarbonylmethyl-4-triethylsilyloxy-2-cyclopenten-1-one

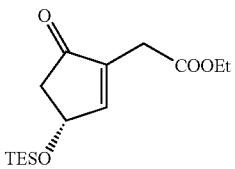

25 g of (R)-2-ethoxycarbonylmethyl-4-hydroxy-2-cyclopenten-1-one (5 g, 98% e.e.) was dissolved in ethyl acetate and the solution was placed in a nitrogen purged flask. Imidazole (13.87 g, 204 mmol) was added. The solution was cooled to 0° C. and triethylchlorosilane (26.6 g, 176 mmol) was added slowly. The reaction mixture was allowed to warm to room temperature and stirred for another 15 hours. After filtration, the filtrate was washed with a saturated sodium bicarbonate solution and a brine solution, respectively, dried over anhydrous magnesium sulfate, and concentrated to obtain the titled compound (38.5 g, 95%). $[\alpha]_D$: +27.8° (c 1.0, $CH_3CN$).

$^1$H-NMR ($CDCl_3$/TMS): δ 7.36 (s, 1H), 4.96 (m, 1H), 4.16 (q, 2H), 3.23 (dd, 2H), 2.84 (dd, 1H), 2.32 (dd, 1H), 1.26 (t, 3H), 0.99 (t, 9H), 0.65 (q, 6H).

Example 37

(R)-2-Hydroxycarbonylmethyl-4-triethylsilyloxy-2-cyclopenten-1-one

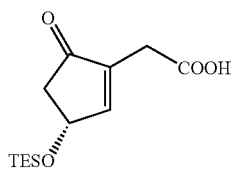

20 g of (R)-2-ethoxycarbonylmethyl-4-triethylsilyloxy-2-cyclopenten-1-one obtained from Example 35 and 2 g of *Candida antarcitica* lipase were suspended in 200 ml of phosphate buffer (10 mM, pH 6.5-7.5) and stirred at room temperature. The pH of the solution was maintained by 1N sodium hydroxide solution and finally adjusted to 7.0 upon completion of the reaction and the Lipase was removed by filtration. The reaction mixture was extracted with 100 ml of ethyl acetate twice. The pH of the aqueous layer was further adjusted to 6.0 using a saturated sodium hydrogensulfate solution. The aqueous layer was extracted twice again using 100 ml of ethyl acetate. The organic layers were combined, dried over anhydrous magnesium sulfate, filtered, and concentrated to obtain (R)-2-hydroxycarbonylmethyl-4-triethylsiloxy-2-cyclopenten-1-one (12 g, 65% yield). $[\alpha]_D$: +19.8° (c 1.0, $CH_3CN$);

$^1$H-NMR ($CDCl_3$/TMS): δ 7.35 (m,1H), 4.93 (m,1H), 3.26 (m, 2H), 2.78 (dd, 1H), 2.31 (dd, 1H), 0.95 (t, 9H), 0.64 (q, 6H).

Example 38

(R)-2-[2-(4-morpholineethoxycarbonylmethyl)]-4-triethylsilyloxy-2-cyclopenten-1-one

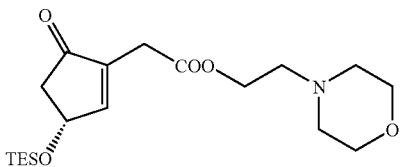

5 g (18.5 mmol) of 2-hydroxycarbonylmethyl-4-triethylsiloxy-2-cyclopen-1-one (21 mmol) obtained from Example 37, 4-(2-hydroxyethyl)-morpholine (2.9 g, 22.1 mmol), dichloromethane (50 ml), and 0.2 g 4-(dimethylamine)-pyridine were added together to a 30 ml dichloromethane solution containing 1,3-dicyclohexylcarbodiimide (6 g, 29 mmol). The reaction mixture was stirred at room temperature for about 4 hours. The precipitate was filtered off. The filtrate was washed with a saturated sodium bicarbonate solution, dried over anhydrous magnesium sulfate, filtered, and evaporated under vacuum. The residue was purified by flash chromatography on silica gel to give the titled compound as an oil (4.4 g, 62%). $[\alpha]_D$: +26.0° (c 1.0, $CH_3CN$);

$^1$H-NMR ($CDCl_3$/TMS): δ 7.40 (m, 1H), 4.97 (m, 1H), 4.28 (t, 2H), 3.75 (t, 4H), 3.28 (q, 2H), 2.80 (dd, 1H), 2.69 (t, 2H), 2.57 (s, 4H), 2.33 (dd, 1H), 1.01 (t, 9H), 0.68 (q, 6H).

Example 39

(R)-2-(2-Cyanoethoxycarbonylmethyl-4-triethylsilyloxy-2-cyclopenten-1-one

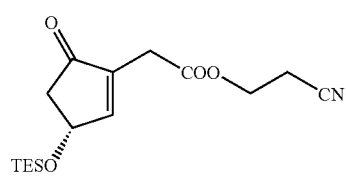

Example 39 was conducted according to the procedure of Example 38 except that 3-hydroxypropionitrile was used in the reaction instead of 4-(2-hydroxyethyl)morpholine. The titled compound was obtained as an oil (yield: 64%).

$[\alpha]_D$: +30.90 (c 1.0, $CH_3CN$); $^1$H-NMR ($CDCl_3$/TMS): δ 7.37 (s, 1H), 4.96 (m, 1H), 4.30 (t, 2H), 3.30 (q, 2H), 2.79 (dd, 1H), 2.72 (t, 2H), 2.31 (dd, 1H), 0.98 (t, 9H), 0.65 (q, 6H).

Example 40

(R)-2-(3-Ethoxycarbonylphenoxycarbonylmethyl)-4-triethylsiloxy-2-cyclopenten-1-one

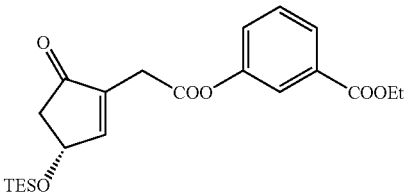

Example 40 was conducted according to the procedure of Example 38 except that ethyl 3-hyrdoxybenzoate was used in the reaction instead of 4-(2-hydroxyethyl)-morpholine. The titled compound was obtained as an oil (yield: 67%). $[\alpha]_D$: +21.0° (c 1.0, $CH_3CN$); $^1$H-NMR ($CDCl_3$/TMS): δ 7.96 (m, 1H), 7.79 (m, 1H), 7.49 (m, 2H), 7.32 (m, 1H), 5.03 (m, 1H), 4.41 (q, 2H), 3.56 (q, 2H), 2.87 (dd, 1H), 2.40 (dd, 1H), 1.43 (t, 3H), 1.03 (t, 9H), 0.70 (q, 6H).

Example 41

2-[(1R,2S,5R)-Menthoxycarbonylmethyl]-(4R)-hydroxy-2-cyclopenten-1-one

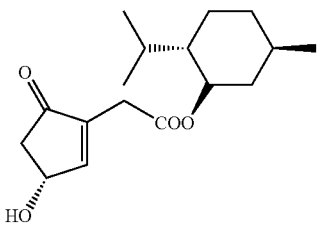

5 g (18.5 mmol) of 2-hydroxycarbonylmethyl-4-triethylsiloxy-2-cyclopen-1-one (21 mmol) obtained from Example 37, (1R, 2S, 5R)-(−)-menthol (3.44 g, 22.0 mmnol), dichloromethane (50 ml), and 0.2 g 4-(dimethylamine)pyridine were added together to a 30 ml dichloromethane solution containing 1,3-dicyclohexylcarbodiimide (6 g, 29 mmol). The reaction mixture was stirred at room temperature for about 4 hours. The precipitate was filtered off. The filtrate was washed with a saturated sodium bicarbonate solution, dried over anhydrous magnesium sulfate, filtered, and evaporated under vacuum. The crude product was dissolved in 50 ml THF and 5 ml water, further added with 1 ml 3N HCl(aq) and stirred for 1 hour at room temperature. Upon completion of the reaction, the reaction mixture was diluted with ethyl acetate and washed with a sodium bicarbonate aqueous solution and a brine solution. The organic liquid was subjected to the previously described work-up procedure, including filtration, and evaporation. The residue was purified by flash chromatography on silica gel to give the titled compound as an oil (4.3 g, 79%).

Example 42

(R)-2-(4-Methoxyphenylmethoxycarbonylmethyl)-4-hydroxy-2-cyclopententen-1-one

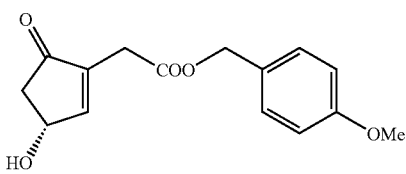

Example 42 was conducted according to the procedure of Example 41 except that 4-methoxybenzyl alcohol was used in the reaction instead of (−)-menthol. The titled compound was obtained as an oil (yield:67%)

$^1$H-NMR (CDCl$_3$/TMS): δ 7.39 (s, 1H), 7.25 (d, 2H), 6.87 (d, 2H), 5.06 (s, 3H), 4.95 (m, 1H), 3.79 (s, 3H), 3.26 (s, 2H), 2.81 (dd, 1H), 2.31 (d, 1H).

Example 43

(R)-2-(2-Naphthoxycarbonylmethyl)-4-tert-butyldimethylsilyloxy-2-cyclopenten-1-one

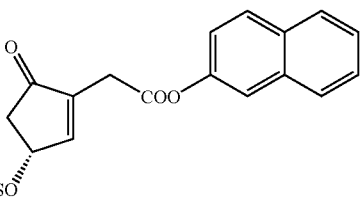

5 g (27.1 mmol, 98% e.e.) of (R)-2-ethoxycarbonylmethyl-4-hydroxy-2-cyclopenten-1-one was dissolved in ethyl acetate and the solution was placed in a nitrogen-purged flask. Imidazole (2.77 g, 40.7 mmol) was added. The solution was cooled to 0° C. and tert-butyldimethylchlorosilane (5.3 g, 35 mmol) was added in portions. The reaction mixture was allowed to warm to room temperature, and stirred for 15 hours. After filtration, the filtrate was washed with a saturated sodium bicarbonate solution and a brine solution, respectively, dried over anhydrous magnesium sulfate, filtered, and evaporated to dryness. The residue and 1 g of *Candida* antartica lipase were suspended in 100 ml of phosphate buffer (10 mM, pH 6.5-7.5) and stirred at room temperature. The pH of the solution was maintained by 1N sodium hydroxide solution and finally adjusted to 7.0 upon completion of the reaction and the Lipase was removed by filtration. The reaction mixture was extracted with 50 ml of toluene twice. The pH of the aqueous layer was further adjusted to 6.0 using a saturated sodium hydrogensulfate solution. The aqueous layer was extracted twice again using 100 ml of ethyl acetate. The organic layers were combined, dried over anhydrous magnesium sulfate, filtered, and concentrated. The residue and 2-naphthol (5.0 g, 34.7 mmol) was dissolved in dichloromethane (50 ml), and 0.2 g 4-(dimethylamine)pyridine were added together to a 30 ml dichloromethane solution containing 1,3-dicyclohexylcarbodiimide (7.5 g, 36 mmol). The reaction mixture was stirred at room temperatures for about 4 hours. The precipitate was filtered off. The filtrate was washed with a saturated sodium bicarbonate solution, dried over anhydrous magnesium sulfate, filtered, and evaporated under vacuum. The residue was purified by flash chromatography on silica gel to give the titled compound as white solid (5.2 g, 48%).

$^1$H-NMR (CDCl$_3$/TMS): δ 7.78 (m, 2H), 7.74 (d, 1H), 7.50 (s, 1H), 7.42 (m, 3H), 7.17 (dd, 1H), 4.95 (m, 1H), 3.50 (q, 2H), 2.77 (dd, 1H), 2.30 (dd, 1H), 0.82 (s, 9H), 0.08 (s, 6H).

Example 44

(R)-2-Hydroxycarbonylmethyl-4-tetrahydropyranyloxy-2-cyclopenten-1-one

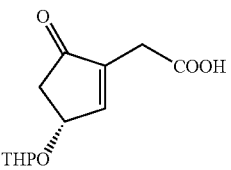

Example 44 was conducted according to the procedures of Example 4 and Example 5 except that optically active 2-ethoxycarbonylmethyl-4-hydroxy-2-cyclopenten-1-one (98% e.e.) was used in the reaction instead of racemic 2-ethoxycarbonylmethyl-4-hydroxy-2-cyclopenten-1-one. The titled compound was obtained as an oil.

Example 45

(R)-2-(2-Naphthoxycarbonylmethyl)-4-tetrahydropyranyloxy-2-cyclopenten-1-one

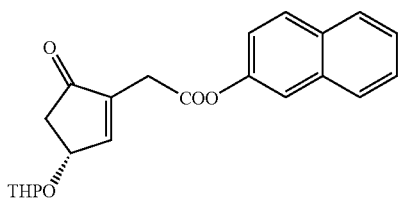

5 g of 2-hydroxycarbonylmethyl-4(R)-tetrahydropyranyloxy-2-cyclopenten-1-one (21 mmol) obtained from Example 44, 2-naphthol (4.7 g, 32 mmol), dichloromethane (50 ml), and 0.2 g 4-(dimethylamine)pyridine were added together to a 50 ml dichloromethane solution containing 1,3-dicyclohexylcarbodiimide (7 g, 34 mmol). The reaction mixture was stirred at room temperature for about 4 hours. The precipitate was filtered off. The filtrate was washed with 20 ml of diluted hydrochloride solution, water, dried over anhydrous magnesium sulfate, filtered, and evaporated under vacuum. The residue was purified by flash chromatography on silica gel to give the titled compound as white solid (3.8g, 64%). MP: 75° C.; $[\alpha]_D$+29.3° (c 1.0, $CH_3CN$); $^1$H-NMR ($CDCl_3$/TMS): δ 7.10~7.90 (m, 8H), 4.72~5.11 (m, 2H), 3.90 (m, 1H), 3.60 (m, 3H), 2.89 (m, 1H), 2.35~2.60 (m, 1H), 1.40~1.92 (m, 6H).

Example 46

2-Menthoxycarbonylmethyl-4(R)-tetrahydropyranyloxy-2-cyclopenten-1-one

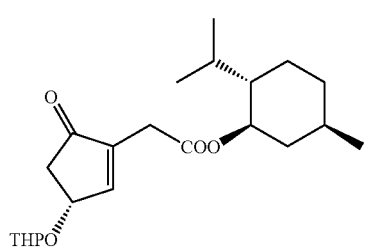

According to the same procedure as described in example 45 except that the equimolar of the substrate used in the reaction was (1R, 2S, 5R)-(−)-menthol instead of 2-naphthol, the titled compound can be prepared and obtained as an oil.

$^1$H-NMR ($CDCl_3$/TMS): δ 7.44~7.58 (m, 1H), 4.65~5.04 (m, 3H), 3.91 (m, 1H), 3.57 (m,1H), 3.24 (m, 2H), 2.74~2.88 (m, 1H), 2.35~2.54 (m, 1H).

Example 47

(R)-2-Diphenylmethoxycarbonylmethyl-4-tetrahydropyranyloxy-2-cyclopenten-1-one

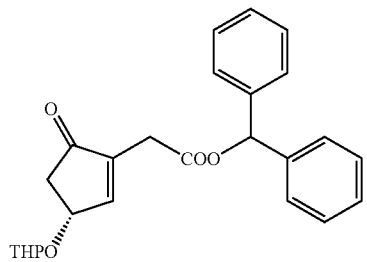

According to the same procedure as described in example 45 except that the equimolar of the substrate used in the reaction was benzhydrol instead of 2-naphthol, the titled compound can be prepared as an oil. $^1$H-NMR ($CDCl_3$/TMS): δ 7.20~7.42 (m, 11H), 6.81 (s, 1H), 4.85 (m, 1H), 4.68 (m, 1H), 3.79 (m, 1H), 3.46 (m, 1H), 3.30 (m, 2H), 2.74 (m, 1H), 2.20~2.41 (m, 1H), 1.15~1.90 (m, 6H).

Example 48

(R)-2-(3,4-Methylenedioxyphenylmethoxycarbonylmethyl)-4-tetrahydropyranyloxy-2-cyclopen-1-one

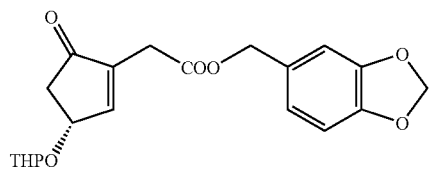

According to the same procedure as described in example 45 except that the equimolar of the substrate used in the reaction is piperonyl alcohol instead of 2-naphthol, the titled compound can be prepared and obtained as an oil.

$^1$H-NMR ($CDCl_3$/TMS): δ 7.42~7.60 (m, 1H), 6.81 (m, 3H), 5.98 (s, 2H), 5.05 (s, 2H), 4.97 (m, 1H), 4.80 (m, 1H), 3.91 (m, 1H), 3.57 (m, 1H), 3.31 (m, 2H), 2.80 (m,1H), 2.30~2.55 (m, 1H), 1.45~2.04 (m, 6H).

We claim:

1. A compound of Formula 1A, which is enriched in the R configuration and has an optical purity of at least 95% enantiomeric excess,

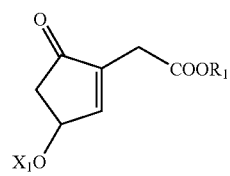

1A wherein

X₁ is H or a protective group for a hydroxy group selected from the group consisting of methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_aR_bR_c$ wherein $R_a$, $R_b$ and $R_c$ are each independently $C_{1-4}$ alkyl, phenyl, benzyl, substituted phenyl, or substituted benzyl; and $R_1$ is (a) aryl or aralkyl, each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, pyridinyl, thiophenyl, furanyl, imidazolyl, morpholinyl, oxazolinyl, piperidinyl, piperazinyl, tetrahydropyranyl, pyrrolidinyl, and pyrrolidinonyl, or (b) menthyl or an unsubstituted $C_3$-$C_{10}$ cycloalkyl.

2. The compound according to claim 1, wherein $R_1$ is aralkyl which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, and alkylaminocarbonyl.

3. The compound according to claim 2, wherein said aralkyl is benzyl which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, and alkylaminocarbonyl.

4. The compound according to claim 3, wherein $R_1$ is benzyl or diphenylmethyl.

5. The compound according to claim 1 wherein said aryl is selected from the group consisting of phenyl, naphthyl, anthryl, and phenanthryl, each of which is unsubstituted or substituted with one or more substituents selected from the group consisting of halogen, alkyl, alkoxyl, thioalkoxyl, cyano, alkoxycarbonyl, arylcarbonyl, arylaminocarbonyl, and alkylaminocarbonyl.

6. The compound according to claim 5, wherein $R_1$ is phenyl, naphthyl, piperonyl, or alkoxycarbonylphenyl.

7. A process for preparing an isolated compound for the synthesis of crystallizable conjugate addition products in a prostaglandin synthesis process, wherein said compound is an R-configuration enriched cyclopentenone having Formula 1 and having an optical purity of at least 95% enantiomeric excess:

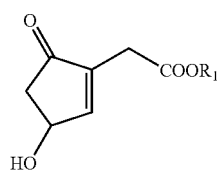

the process comprising the steps of:

(a) enantioselectively (R)-esterifying a racemic alcohol mixture of the compound of Formula 1 with an acyl donor and a first lipase thereby obtaining a mixture of first (R)-ester and an unreacted (S)-alcohol;

(b) removing from the mixture the unreacted (S)-alcohol; and then (c) deacylating the (R)-ester with a second lipase in the presence of an alcohol of formula $R_1OH$ or with a catalyst in the presence of an alcohol of formula $R_1OH$, thereby obtaining said isolated compound, wherein in each of the compound of Formula 1 and the $R_1OH$ alcohol, $R_1$ is selected from the group consisting of:

(a) aryl or aralkyl, each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, pyridinyl, thiophenyl, furanyl, imidazolyl, morpholinyl, oxazolinyl, piperidinyl, piperazinyl, tetrahydropyranyl, pyrrolidinyl, and pyrrolidinonyl, or (b) menthyl or an unsubstituted $C_3$-$C_{10}$ cycloalkyl.

8. The process according to claim 7, wherein removing the unreacted (S)-alcohol comprises converting the unreacted (S)-alcohol to the (R)-ester by reacting the (S)-alcohol with an acyloxy donor in the presence of a dialkylazodicarboxylate and a triarylphosphine.

9. The process according to claim 7, wherein the acyl donor is vinyl acetate, isopropenyl acetate, vinyl valerate, isopropenyl valerate, vinyl butyrate, or isopropenyl butyrate.

10. The process according to claim 7, wherein the first lipase is obtained from *Candida antarctica, Achromobacter spp, Alcaligenese spp, Pseudomonas fluorescens, Pseudomonas stutzri*, or *Pseudomonas cepacia*.

11. The process according to claim 8, wherein the acyloxy donor is a carboxylic acid.

12. The process according to claim 7, wherein the dialkylazodicarboxylate is diethylazodicarboxylate, diisopropylazodicarboxylate, or dibenzylazodicarboxylate.

13. The process according to claim 7, wherein the triarylphosphine is triphenylphosphine.

14. The process according to claim 7, wherein the second lipase comprises a lipase obtained from *Pseudomonas spp, Achromobacter spp*, or *Candida antarctica*.

15. The process according to claim 7, wherein the second lipase comprises a lipase obtained from *Candida antarctica*.

16. The process according to claim 7, wherein the catalyst comprises an acid selected from the group consisting of phosphoric acid, p-toluenesulfonic acid, hydrobromic acid, hydrochloric acid, nitric acid, sulfuric acid, and mixtures thereof.

* * * * *